United States Patent [19]
Ueno

[11] Patent Number: 5,871,455
[45] Date of Patent: Feb. 16, 1999

[54] OPHTHALMIC APPARATUS

[75] Inventor: Yasunori Ueno, Kawasaki, Japan

[73] Assignee: Nikon Corporation, Tokyo, Japan

[21] Appl. No.: 838,998

[22] Filed: Apr. 23, 1997

[30] Foreign Application Priority Data

Apr. 30, 1996 [JP] Japan .................................. 8-132692

[51] Int. Cl.$^6$ ............................................... A61B 5/103
[52] U.S. Cl. ............................................ 600/587; 351/211
[58] Field of Search ................................. 351/211, 212; 600/558

[56] References Cited

U.S. PATENT DOCUMENTS

| | | | |
|---|---|---|---|
| 5,500,697 | 3/1996 | Fujieda | 351/212 |
| 5,555,039 | 9/1996 | Iki et al. | 351/212 |
| 5,576,780 | 11/1996 | Yancey | 351/211 |
| 5,625,428 | 4/1997 | Isogai | 351/208 |
| 5,684,562 | 11/1997 | Fujieda | 351/212 |

*Primary Examiner*—Max Hindenburg
*Assistant Examiner*—Pamela L. Wingood
*Attorney, Agent, or Firm*—Chapman and Cutler

[57] ABSTRACT

An ophthalmic apparatus having a smaller size while guaranteeing a required optical performance from each optical system component is provided. The ophthalmic apparatus includes a fogging optical system for removing an accommodation power of an eye being examined so that the eye is properly relaxed. A detecting optical system is used for detecting information relating to the eye being examined. The fogging optical system and the detecting optical system share a common lens group containing at least one cemented lens. Positive and negative lenses are included in the cemented lens. The common lens group, as a whole, has a positive refractive power.

5 Claims, 6 Drawing Sheets

SPHERICAL ABERRATION

FIG. 2b

ASTIGMATISM

FIG. 2c

COMA

FIG. 2d

DISTORTION

FIG. 3a

SPHERICAL ABERRATION

FIG. 3b

ASTIGMATISM

FIG. 3c

COMA

FIG. 3d

DISTORTION

OPHTHALMIC APPARATUS

BACKGROUND OF THE INVENTION

1. Field of the Invention

This invention relates to an ophthalmic apparatus having what is referred to as a "fogging" optical system and a detecting optical system.

2. Description of Related Art

Figure 6:
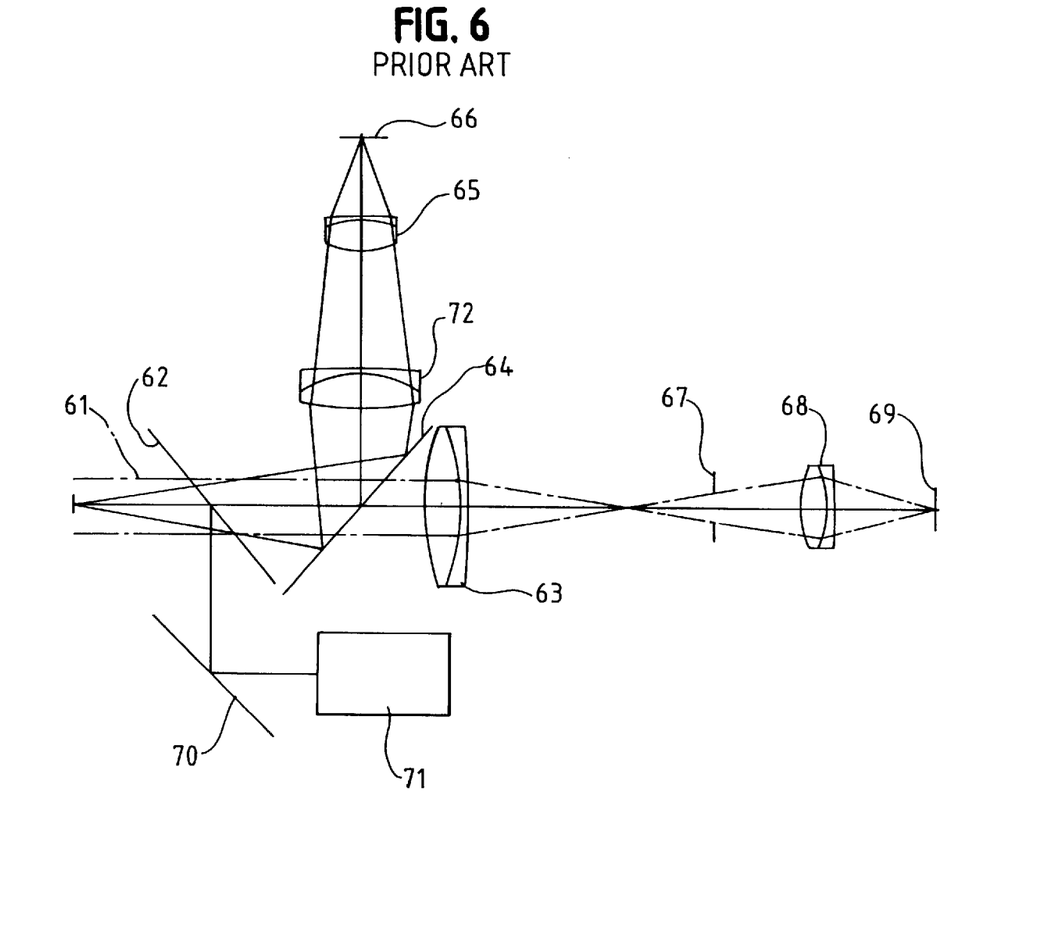
FIG. 6, as noted above, is a schematic illustration of a conventional eye refractive power apparatus.

FIG. 6 is a schematic diagram illustrating the structure of a conventional ophthalmic apparatus such as an eye refractive power measurement apparatus.

In the ophthalmic apparatus shown in FIG. 6, visible light from a gazing target 69 passes through a projecting lens 68, a stop 67, a lens 63, and half mirrors 64 and 62. This visible light then reaches an eye 61 to be examined. An image of the gazing target 69 is formed on the retina of the eye 61. The gazing target 69, the projecting lens 68, the stop 67, and the lens 63 together form a fogging optical system for relaxing the eye 61 for proper examination.

The ophthalmic apparatus shown in FIG. 6 has an eye refractive power measurement optical system 71 for measurement of the refractive power of the eye 61 to be examined. Infrared (IR) light for measurement is emitted from the eye refractive power measurement optical system 71 and reflected by a mirror 70 and a half mirror 62. The IR light is projected on the fundus of the eye 61 for examination and then reflected from the fundus of the eye 61. A portion of the IR light goes back along the optical path having the half mirror 62 and the mirror 70 and is incident on a light-receiving element located inside of the eye refractive power measurement optical system 71. The refractive power of the eye 61 is measured based on the photoelectric output of the light-receiving element.

The IR light reflected from the eye 61 is also partially transmitted through the half mirror 62 and reflected by the half mirror 64. The light reflected by the half mirror 64 passes through an image-forming lens system including a lens 72 and a lens 65. This light forms an image of the eye 61 on an image pickup plane 66. In this way, the lens 72, the lens 65, and the image pickup plane 66 together form an image pickup optical system for detecting image information relating to the eye 61 undergoing examination.

When a fogging optical system is used for removing the accommodation power of an eye under examination, the diameter of the human pupil is small and the F-number is relatively large. The field angle is relatively large in order to alleviate instrumental myopia influences. In the image pickup optical system for observing the eye and the ophthalmic measurement optical system for measurement of refractive power information of the eye, however, the F-number is relatively small in order to guarantee the provision of a prescribed light amount. The field angle (or the height of the object) is also relatively small. Optical systems having properties entirely different from each other, therefore, coexist in the ophthalmic measurement and other ophthalmic apparatuses.

When efforts are made to reduce the sizes of ophthalmic apparatuses having these optical systems, reductions in the focal lengths of various lens groups forming each optical system may be used. However, in order to reduce the focal lengths of the various lens groups while ensuring the desired optical characteristics for each optical system, the number of lenses forming each lens group becomes larger. This is a disadvantage.

SUMMARY OF THE INVENTION

It is an object of this invention to provide a type of ophthalmic apparatus that permits a reduction in an apparatus size, has a simple constitution, and guarantees a desired optical performance for each optical system.

This invention provides a type of ophthalmic apparatus in which a fogging optical system is used for removing the accommodation power of the eye being examined and realizes eye relaxation. A detecting optical system is also used for detecting information relating to the eye being examined. The fogging optical system and the detecting optical system share a common lens group. The common lens group contains at least one cemented lens. The cemented lens includes a positive lens Lp and a negative lens Ln and, as a whole, has a positive refractive power.

In a preferred embodiment of this invention, the cemented lens includes, from the side of the apparatus closest to the eye being examined, a positive lens Lp and negative lens Ln cemented to each other. It is preferred that the cemented lens have a convex surface facing the side of the system closest to the eye being examined.

Supposing that the radius of curvature of the non-cemented optical surface of the positive lens Lp is r1, the radius of curvature of the non-cemented optical surface of the negative lens Ln is r2, the refractive index of the positive lens Lp with respect to the d-line is n1, the refractive index of the negative lens Ln with respect to the d-line is n2, the Abbe number of the positive lens Lp is $\sigma_1$, and the Abbe number of the negative lens Ln is $\sigma_2$, it is preferred that the following conditions be met:

$$0 < (r2+r1)/(r2-r1) < 0.2$$

$$0.05 < |n1-n2| < 0.25$$

$$15 < \sigma 1 - \sigma 2 < 30$$

Again, the image pickup optical system, the eye refractive power measurement optical system or other optical system for detecting information relating to the eye under examination, and the fogging optical system for relaxing the eye under examination share the common lens group. The common lens group, again, includes at least one cemented lens Lj having the positive lens Lp and the negative lens Ln.

Since the various optical systems forming the ophthalmic apparatus share a common lens group having a certain structure, it is possible to reduce the size of the apparatus and to cut costs while guaranteeing that the various optical systems have a desired optical performance.

Forming the cemented lens, from the side of the system closest to the eye being examined, of the positive lens Lp and the negative lens Ln cemented to each other helps to eliminate chromatic aberration.

In order to eliminate spherical aberration, it is preferred to form the cemented lens Lj with a convex surface facing the eye undergoing examination.

An explanation will now be given of various formulas defining proper conditions according to this invention. It is preferred that the following conditions (1)–(3) be satisfied.

$$0 < (r2+r1)/(r2-r1) < 0.2 \qquad (1)$$

$$0.05 < |n1-n2| < 0.25 \qquad (2)$$

$$15 < \sigma 1 - \sigma 2 < 30 \qquad (3)$$

In equations (1), (2) and (3), r1 is the radius of curvature of the non-cemented optical surface of the positive lens Lp;

r2 is the radius of curvature of the non-cemented optical surface of the negative lens Ln;

n1 is the refractive index of the positive lens Lp with respect to the d-line;

n2 is the refractive index of the negative lens Ln with respect to the d-line;

$\sigma_1$ is the Abbe number of the positive lens Lp; and $\sigma_2$ is the Abbe number of the negative lens Ln.

Condition (1) specifies parameters which should be met for proper correction of spherical aberration and coma. In a fogging optical system, the F-number is relatively large. Consequently, the spherical aberration and coma generated are not very large. On the other hand, in an image pickup optical system or an eye refractive power measurement optical system, since the F-number is relatively small, the spherical aberration and coma tend to be significant.

If the range defined by the upper limit and the lower limit in condition (1) is not satisfied, then a proper correction for spherical aberration and coma in the image pickup optical system and the eye refractive power measurement system is not possible.

Condition (2) specifies parameters which should be met for proper correction of distortion and astigmatism.

In the image pickup optical system and the eye refractive power measurement system, the field angle is relatively small. Consequently, in these systems, no significant distortion or astigmatism is present. On the other hand, in the fogging optical system, since the field angle is relatively large, distortion and astigmatism are typically present.

If the range defined by the upper limit and lower limit in condition (2) is not satisfied, then, in the fogging optical system, proper correction for distortion and astigmatism is impossible.

Satisfaction of condition (3) ensures a proper correction for chromatic aberration.

In the image pickup optical system, the eye refractive power measurement system, and the fogging optical system, both longitudinal and lateral chromatic aberrations take place. In order to properly correct for the chromatic aberrations, it is preferred that the range defined by the upper and lower limits in condition (3) be satisfied. Even when this range is not satisfied, the chromatic aberration can still be corrected to a certain degree in each optical system. In the other lens systems, however, the curvature of the cemented surface increases and the tolerance becomes smaller. Consequently, manufacturing becomes more difficult and the number of lenses increases.

DESCRIPTION OF THE PREFERRED EMBODIMENTS

This invention will now be explained, in detail, with reference to the embodiments illustrated by the drawing figures.

Figure 1:
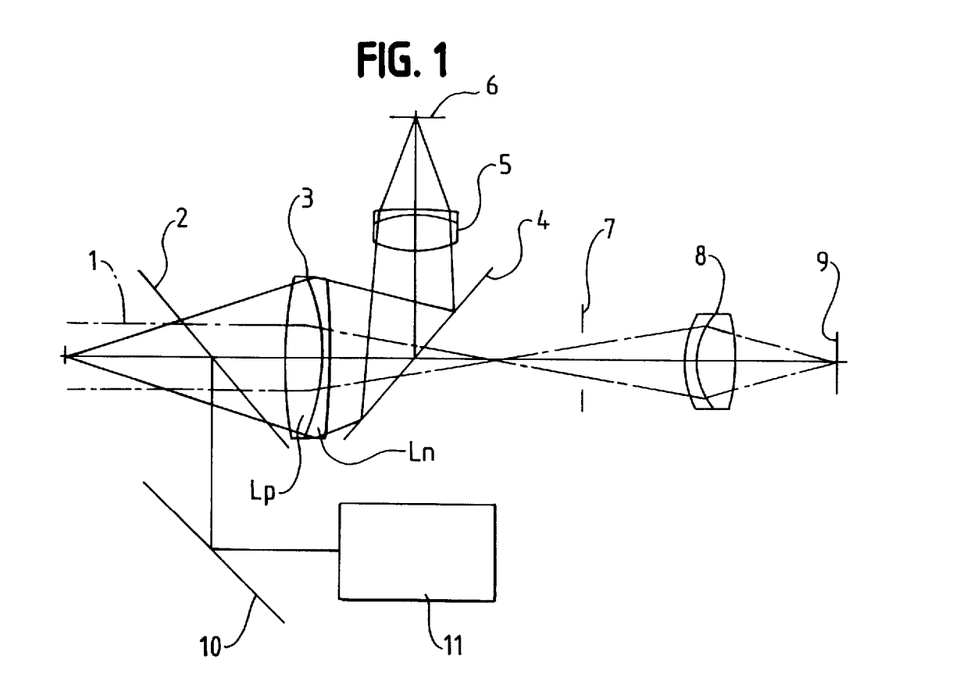
FIG. 1 is a schematic illustration of an ophthalmic apparatus according to a first embodiment of this invention.
Figure 2A:
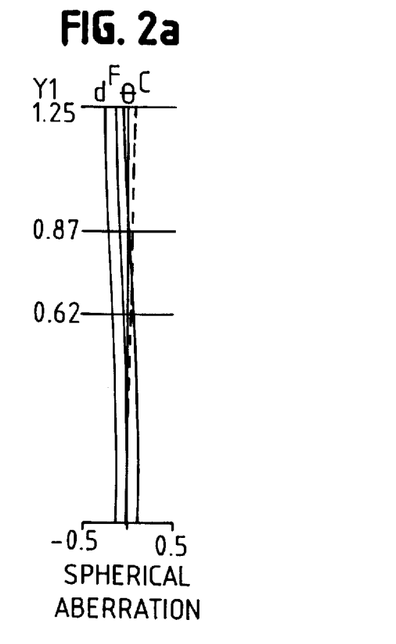
FIG. 2 shows diagrams illustrating various aberrations in the fogging optical system of the first embodiment.
Figure 2B:
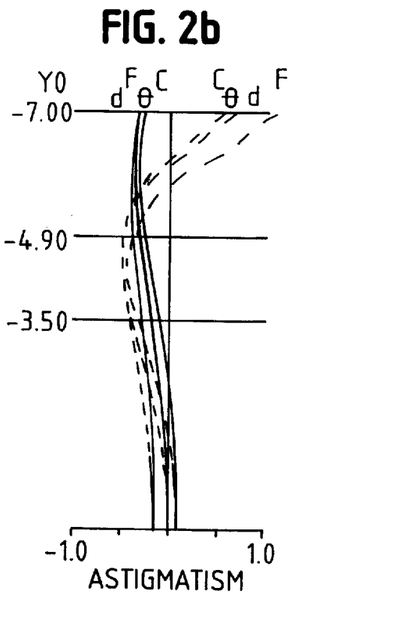
Figure 2C:
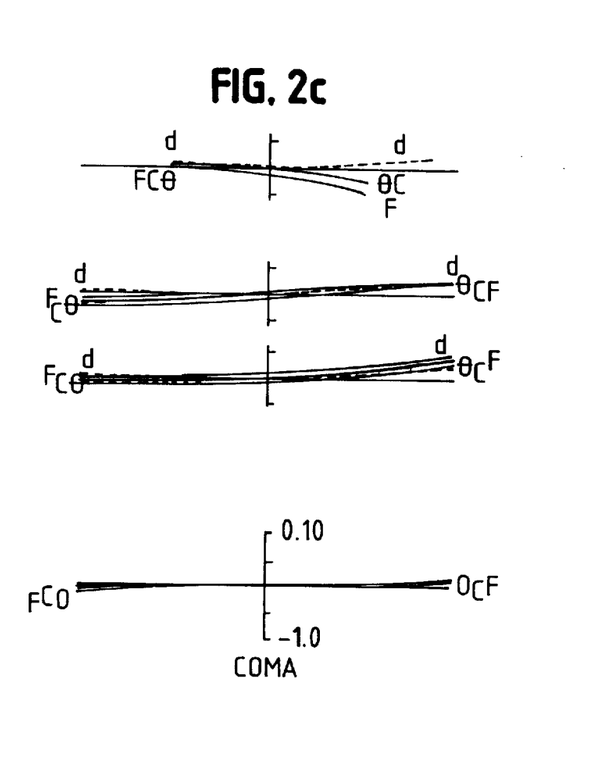
Figure 2D:
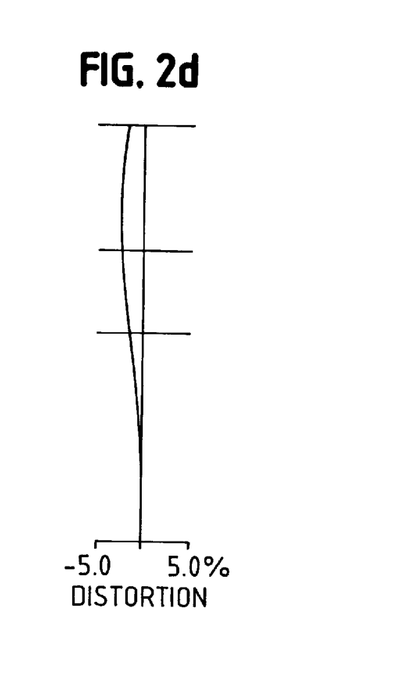
Figure 3A:
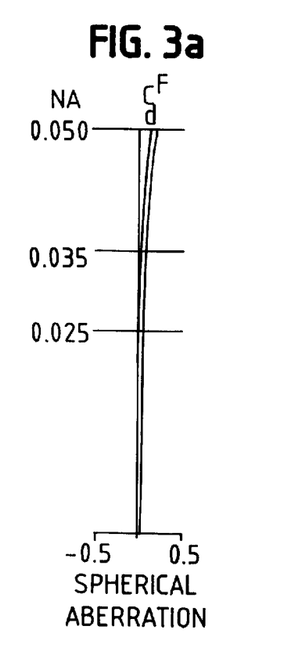
FIG. 3 shows diagrams illustrating various aberrations in the image pickup optical system of the first embodiment.
Figure 3B:
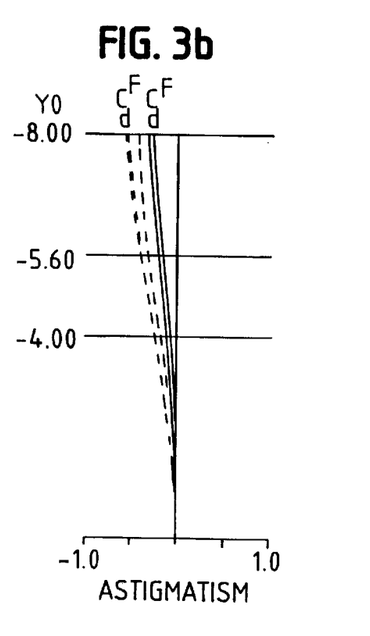
Figure 3C:
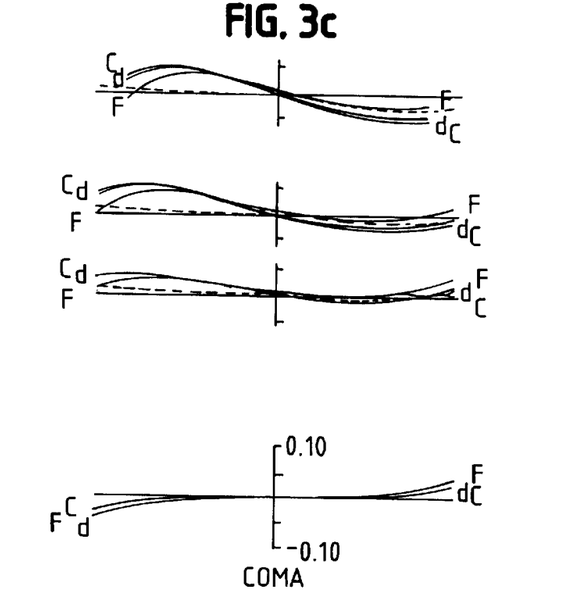
Figure 3D:
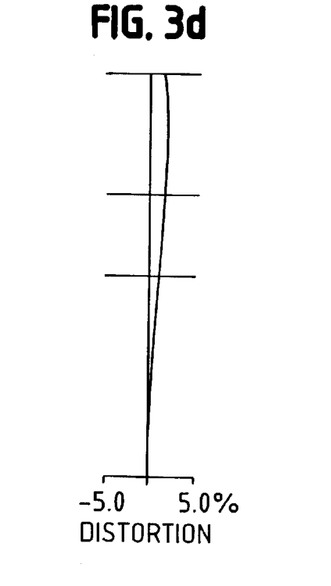

FIG. 1, as noted above, is a schematic diagram illustrating the structure of an ophthalmic apparatus according to a first embodiment. The first embodiment is an application of the invention in an eye refractive power measurement apparatus having a fogging optical system, an image pickup optical system, and an eye refractive power measurement optical system. Also, in FIG. 1, the internal construction of the eye refractive power measurement optical system 11 is omitted. The eye refractive power measurement optical system 11 may utilize what is referred to as retinoscopy, in which the eye refractive power is measured by detecting the speed of movement of a shadow on the pupil. An objective ocular refractive power measurement system using the method of retinoscopy is disclosed, for example, in Japanese Laid-Open Patent Application No. 55-86,437.

The eye refractive power measurement optical system 11 shown in FIG. 1 is used for measuring the refractive power of an eye 1 under examination and contains a light source emitting IR light to measure the eye refractive power. The IR light emanating from the eye refractive power measurement optical system 11 forms an image on the pupil plane of the eye 1 under examination. The fundus of the eye under examination is scanned by the beam of light. The light reflected from the eye 1 is received, as an image of the pupil plane of the eye 1, by a light-receiving element contained in the eye refractive power measurement optical system 11. The refractive power of the eye 1 under examination is measured based on the photoelectric output of the light-receiving element using conventional technology.

The ophthalmic apparatus shown in FIG. 1 has a fogging system for removing the accommodation power of the eye 1 under examination so as to relax the eye. The automatic fogging system has a visible-light source (not shown in the figure) for illuminating a gazing target 9 with visible light. The visible light reflected from the gazing target 9 passes through a projecting lens 8 and a stop 7, transmits through a half mirror 4, and is incident on a cemented lens 3. After passing through the half mirror 4, the light from the gazing target 9 traveling through the cemented lens 3 is transmitted through a half mirror 2. This transmitted light is incident on the pupil of the eye 1 under examination. The light is then transmitted through the crystalline lens of the eye and is projected onto the retina. In this way, an image of the gazing target 9 is formed on the retina of the eye 1 under examination. There is also a light source (not shown in the figure) in the apparatus shown in FIG. 1 for illuminating the anterior portion of the eye 1 under examination.

If the refractive state of the eye 1 under examination is constant, then the position of the image of the gazing target 9 formed on the retina of the eye 1 will be at a specific single point on the optical axis. A one-to-one correspondence between the position of the image of the gazing target 9 formed on the retina of the eye 1 and the refractive power of the eye 1 under examination is present. On the other hand, when the eye 1 under examination is allowed to relax, it is necessary to form the image of the gazing target at a position which is slightly in front of the retina so that the eye 1 is oriented toward a far point. Consequently, the position of the gazing target 9 can be appropriately adjusted. It is also possible to eliminate the accommodation power of the eye 1 and to allow the eye 1 to relax.

The fogging optical system includes, from the side of the apparatus closest to the eye under examination, the cemented lens 3 and the projecting lens 8.

The ophthalmic apparatus shown in FIG. 1 also has an image pickup optical system for detecting image information relating to the eye 1 under examination. In this image pickup optical system, the light reflected from the eye 1 (such as the light for illuminating the anterior portion of the eye) passes along the optical path in which the half mirror 2 and the cemented lens 3 are disposed and is incident on the half mirror 4. The light reflected by the half mirror 4 goes through the image-forming lens 5. An image of the eye 1 is formed on an image pickup plane 6 by an image-forming lens 5. Based on the detected image of the eye under examination, the operator of the apparatus can check to see that there is no deviation in position between the eye 1 and the main body of the apparatus. The operator can also determine that there are no eyelashes of the patient or other obstructions in the measurement optical path.

The image pickup optical system includes, from the side of system adjacent to the eye under examination, the cemented lens 3 and the image-forming lens 5.

In the ophthalmic apparatus of the first embodiment, after checking the position deviation between the eye 1 and the apparatus main body with the image pickup optical system, the refractive power of the eye 1 can be measured by using the eye refractive power measurement system 11 while the eye 1 is relaxed by using the fogging optical system. The fogging optical system and the image pickup output system share the cemented lens 3. The cemented lens 3 shared by the two optical systems is a cemented biconvex lens that includes, from the side of system closest to the eye being examined, a positive lens Lp and a negative lens Ln.

In Table I, values of various parameters of the fogging optical system and the image pickup optical system, and values corresponding to certain conditions in the first embodiment, are listed.

In Table I, the left-side number represents the lens surface number, counting from the side of the system closest to the eye under examination. The letter r represents the radius of curvature, in mm, of the lens surface. The letter d represents the distance, in mm, between the lens surfaces. The letter n and the character σ represent the refractive index and Abbe number, at the d-line (─=587.63 nm), respectively.

TABLE I

Data for the fogging optical system

| | r | d | n | ν | |
|---|---|---|---|---|---|
| | | 87.6 | | | Eye 1 under examination |
| 1 | 39.0 | 7.5 | 1.658 | 50.8 | Cemented lens 3 |
| 2 | −17.9 | 2.0 | 1.795 | 28.6 | |
| 3 | −47.9 | 68.5 | | | |
| 4 | ∞ | 18.3 | | | Stop 7 |
| 5 | 21.4 | 1.0 | 1.795 | 28.6 | Projecting lens 8 |
| 6 | 8.5 | 4.0 | 1.658 | 50.8 | |
| 7 | −21.4 | 31.0 | | | |

Data for the image pickup optical system

| | r | d | n | ν | |
|---|---|---|---|---|---|
| | | 87.6 | | | Eye 1 under examination |
| 1 | 39.0 | 7.5 | 1.658 | 50.8 | Cemented lens 3 |
| 2 | −17.9 | 2.0 | 1.795 | 28.6 | |
| 3 | −47.9 | 36.2 | 1.000 | | |
| 4 | 7.2 | 3.5 | 1.589 | 61.1 | Image-forming lens 5 |
| 5 | −5.6 | 1.0 | 1.805 | 25.3 | |
| 6 | −38.5 | 7.2 | | | |

Values corresponding to conditions (1) $(r2 + r1) / (r2 - r1) = 0.102$
(2) $|n1 - n2| = 0.137$
(3) $\nu1 - \nu2 = 22.2$ FIG. 2 illustrates various aberrations in the fogging optical system of the first embodiment. FIG. 3 represents various aberrations in the image pickup optical system of the first embodiment. In both of these figures, ray tracing is made from the side of the system nearest the eye under examination.

In each diagram illustrating the aberrations, Y1 represents, in mm, the incident height, Y0 represents either the incident angle, in degrees (in the fogging optical system), or the height, in mm, of the object (in the image pickup optical system), NA stands for the numerical aperture, d represents the d-line (─=587.6 nm), C represents the C-line (─=65.6.3 nm), and F represents the F-line (─=486.1 nm). In the aberration diagram illustrating astigmatism, the broken line represents the meridional image plane while the solid line represents the sagittal image plane.

As can be seen from these aberration diagrams, the various aberrations in both the fogging optical system and the image pickup optical system can be properly compensated for in the first embodiment. Since the fogging optical system and the image pickup optical system share the cemented lens 3, the size of the apparatus can be reduced and the desired optical performance of the fogging optical system and the image pickup optical system is achieved.

Figure 4:
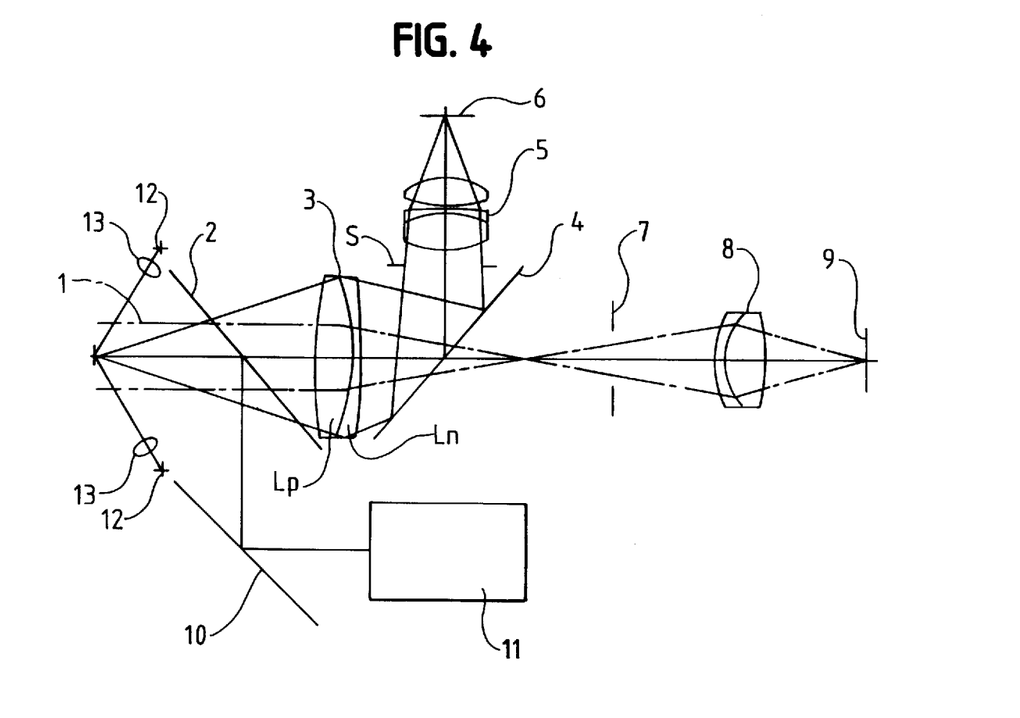
FIG. 4 is a schematic illustration of an ophthalmic apparatus according to a second embodiment of this invention.
Figure 5A:
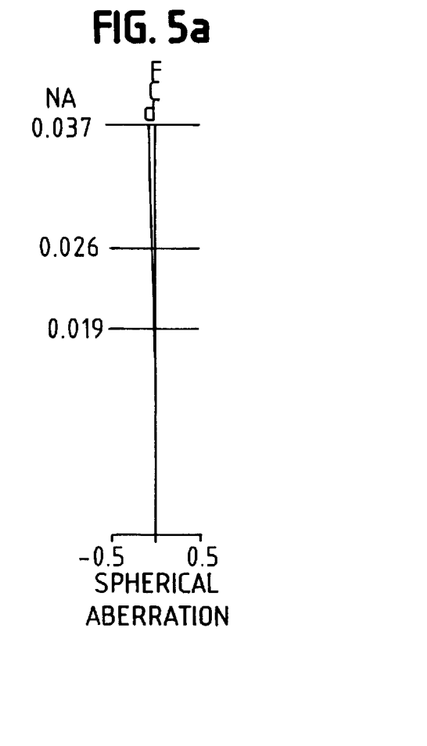
FIG. 5 shows diagrams illustrating various aberrations in the cornea radius of curvature measurement optical system of the second embodiment.
Figure 5B:
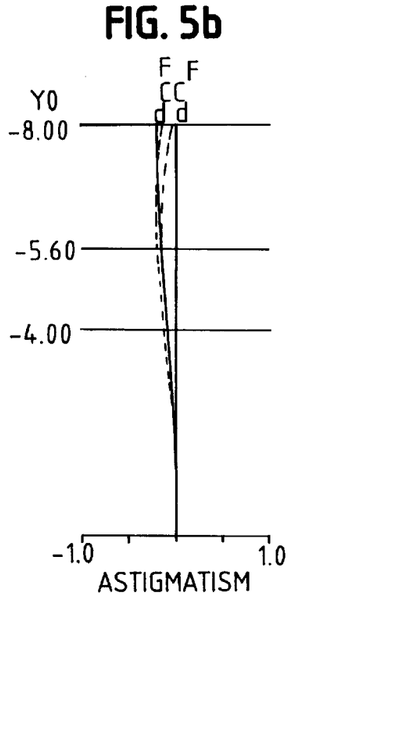
Figure 5C:
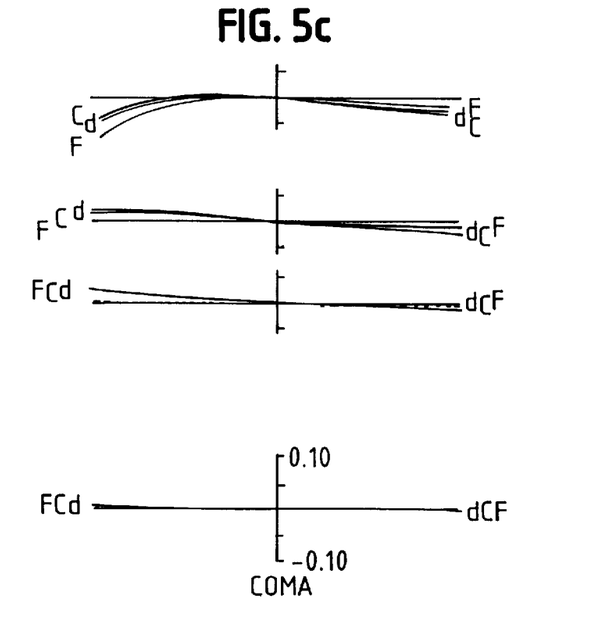
Figure 5D:
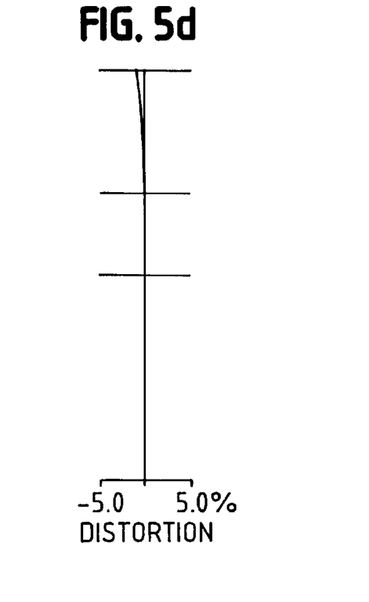

FIG. 4 is a schematic diagram illustrating the construction of the ophthalmic apparatus according to the second embodiment of this invention. The second embodiment is one in which the invention is applied in an eye refractive power/cornea radius of curvature measurement apparatus having a fogging optical system, an image pickup/optical system, a corneal radius of curvature measurement optical system, and an eye refractive power measurement optical system. In the second embodiment, the cornea radius of curvature measurement apparatus is also used as the image pickup optical system for picking up an image of the eye being examined. This feature renders the second embodiment different from the first embodiment. In FIG. 4, elements having the same functions as those shown in FIG. 1 are represented by the same symbols as those used in FIG. 1. The second embodiment will be explained with reference to the points in which it differs from the first embodiment.

The ophthalmic apparatus shown in FIG. 4 has a corneal radius of curvature measurement optical system for measuring the radius of curvature of the cornea of an eye 1 under examination. The corneal radius of curvature measurement optical system has a pair of light sources 12 emitting light for measurement of the radius of curvature of the cornea. The light emitted from each light source 12 is collimated, to form a parallel beam of light, by a collimating lens 13. The parallel beams of light are obliquely incident on the cornea of the eye 1 under examination at prescribed angles. Via the cornea of eye 1 under examination, a virtual image is formed. After the pair of beams of light reflected by the cornea pass through the optical path having the half mirror 2 and the cemented lens 3, they are incident on half mirror 4. The pair of beams of light reflected by the half mirror 4 pass through a stop S and the image-forming lens 5, and are incident on the image pickup plane 6. Based on the distance between the pair of beams of light on the image pickup plane 6, it is possible to measure the radius of curvature of the cornea of the eye 1 under examination. Also, while not shown in the figure, it is preferred that another pair of light sources be provided for measurement of the radius of curvature of the cornea along the direction perpendicular to the paper surface. This other pair of light sources is provided for the measurement of astigmatism.

The cornea radius of curvature measurement optical system, which also acts as an image pickup optical system for picking up an image of the eye undergoing examination, includes, from the side of the system closest to the eye under examination, the bonded lens 3 and the image-forming lens 5. Also, in the cornea radius of curvature measurement optical system, the stop S is placed at the rear focal point of the cemented lens 3 and at the front focal point of the image-forming lens 5. In the cornea radius of curvature measurement optical system shown in FIG. 4, a telecentric optical system is formed.

The fogging optical system and the cornea radius of curvature measurement optical system of the second embodiment share the cemented lens 3. The cemented lens 3, shared by the two optical systems, is a biconvex lens including, from the side of the system closest to the eye under examination, a positive lens Lp and a negative lens Ln.

Table II lists values of various parameters of the cornea radius of curvature measurement optical system of the second embodiment. Values of the parameters for the fogging optical system and for the conditions in the second embodiment are the same as those in the first embodiment as represented in Table I.

In Table II, the left-side number represents the lens surface number counting from the side of the system closest to the eye under examination. The letter r represents the radius of curvature, in mm, of the lens surface. The letter d represents the distance, in mm, between lens surfaces. The letter n and the character σ represent the refractive index and Abbe numbers at the d-line ($\lambda$=587.63 nm), respectively.

TABLE II

Data of the cornea radius of curvature measurement optical system

| | r | d | n | ν | |
|---|---|---|---|---|---|
| | | 87.6 | | | Eye 1 under examination |
| 1 | 39.0 | 7.5 | 1.658 | 50.8 | Cemented lens 3 |
| 2 | −17.9 | 2.0 | 1.795 | 28.6 | |
| 3 | −47.9 | 36.7 | | | |
| 4 | ∞ | 7.3 | | | Stop 5 |
| 5 | 8.0 | 4.0 | 1.519 | 64.1 | Image-forming lens 5 |
| 6 | −5.5 | 1.0 | 1.740 | 28.2 | |
| 7 | −50.4 | 0.2 | | | |
| 8 | 25.3 | 2.1 | 1.603 | 60.6 | |
| 9 | −11.7 | 4.1 | | | |

FIG. 5 illustrates various aberrations in the eye-under-examination image pickup optical system/corneal radius of curvature measurement optical system of the second embodiment. Ray tracing is made from the side of system adjacent to the eye under examination.

In each diagram illustrating the aberrations, Y0 represents, in mm, the height of the object (in the pickup optical system), NA stands for the numerical aperture, d represents the d-line ($\lambda$=587.6 nm), C represents the C-line ($\lambda$=65.63 nm), and F represents the F-line ($\lambda$=486.1 nm). In the aberration diagram illustrating astigmatism, the broken line represents the meridional image plane while the solid line represents the sagittal image plane.

As can be seen from these aberration diagrams, the various aberrations in both the fogging optical system and the cornea radius of curvature measurement optical system can be properly compensated for in the second embodiment. Since the fogging optical system and the image pickup optical system share the cemented lens 3, the size of the apparatus can be reduced and the desired optical performance of the fogging optical system and the cornea radius of curvature measurement optical system is achieved.

Retinoscopy has been mentioned as an appropriate measurement principle of the eye refractive power measurement system. However, retinoscopy is one of various measurement principles which is usable in the eye refractive power measurement system. This invention is not limited to the use of retinoscopy; other measurement principles may also be adopted.

In the first embodiment, the image pickup optical system and the eye refractive power measurement optical system are formed as two independent optical systems. However, it is also possible to have the eye refractive power measurement optical system function as an image pickup optical system.

In the second embodiment, a corneal radius of curvature measurement optical system is utilized as the detecting optical system. However, it is also possible to use a cornea-diameter measurement optical system for measuring the diameter of the cornea as the detecting optical system.

This invention provides a type of ophthalmic apparatus that guarantees a desired optical performance with respect to each optical system while reducing the overall size of the apparatus.

I claim:

1. An ophthalmic apparatus, comprising:
   a fogging optical system for eliminating an accommodation power of an eye being examined so as to realize relaxation;
   a detecting optical system for detecting information relating to the eye being examined; and
   at least one cemented lens, including a positive lens and a negative lens, which, as a whole, has a positive refractive power, said at least one cemented lens forming at least part of a common lens group shared by said fogging optical system and said detecting optical system,
   satisfying the following conditions:

$$0 < (r2+r1)/(r2-r1) < 0.2;$$

$$0.05 < 1n1-n2 < 0.25;$$

$$15 < \sigma 1 - \sigma 2 < 30$$

wherein r1 is a radius of curvature of a surface of said positive lens other than the cemented surface, r2 is a radius of curvature of a surface of said negative lens, other than the cemented surface, n1 is a refractive index of said positive lens with respect to the d-line, n2 is a refractive index of said negative lens with respect to the d-line, σ1 is Abbe number if said positive lens, and σ2 is Abbe number of said negative lens.

2. The ophthalmic apparatus defined in claim 1, wherein the detecting optical system is a telecentric optical system.

3. The ophthalmic apparatus defined in claim 2, wherein the detecting optical system detects corneal information of the eye being examined.

4. The ophthalmic apparatus defined in claim 1, wherein the detecting optical system detects a refractive power of the eye being examined.

5. The ophthalmic apparatus defined in claim 1, wherein the detecting optical system acts as an image pickup optical system for observing the eye being examined.

\* \* \* \* \*